United States Patent [19]

Miyata

[11] 4,068,003

[45] Jan. 10, 1978

[54] METHOD OF MEDICAL TREATMENT OF MYASTHENIA

[75] Inventor: Makoto Miyata, Sapporo, Japan

[73] Assignee: Eisai Co., Ltd., Tokyo, Japan

[21] Appl. No.: 767,059

[22] Filed: Feb. 9, 1977

[30] Foreign Application Priority Data

Feb. 14, 1976 Japan .................................. 51-14416

[51] Int. Cl.² ...................... A61K 31/12; A61K 37/48
[52] U.S. Cl. ........................................ 424/331; 424/94
[58] Field of Search ................................. 424/94, 331

[56] References Cited

U.S. PATENT DOCUMENTS

| | | | |
|---|---|---|---|
| 3,110,373 | 12/1963 | Grim | 424/94 |
| 3,313,781 | 5/1967 | Umehara | 424/94 |
| 3,421,625 | 2/1969 | Shigeta et al. | 424/94 |
| 3,531,437 | 10/1970 | Matsumura | 424/94 |

*Primary Examiner*—Stanley J. Friedman
*Attorney, Agent, or Firm*—Blanchard, Flynn, Thiel, Boutell & Tanis

[57] ABSTRACT

The invention relates to a new use of Coenzyme Q compounds, and more particularly, to a method of medical treatment of myasthenia by administering Coenzyme Q compounds.

5 Claims, No Drawings

METHOD OF MEDICAL TREATMENT OF MYASTHENIA

BACKGROUND OF THE INVENTION

1. Field of the Invention

This invention relates to a method for the treatment of myasthenia which comprises administering to a human suffering from myasthenia a therapeutically effective amount of Coenzyme Q represented by the following general formula:

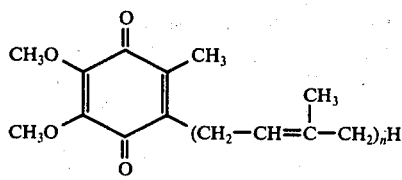

wherein $n$ represents an integer from 7 to 10.

2. Description of the Prior Art

Coenzyme Q is also called, "ubiquinone".

Coenzymes Q were found in lipids of mitochondria in the heart of oxen by Crane at the University of Wisconsin in 1957. Coenzymes Q having various numbers for $n$ in the above general formula are present in the natural world. Although the functions of the Coenzymes Q in vivo have not been known sufficiently, it is generally considered that they take part in the electron transport system in mitochondria. As for medical uses of Coenzymes Q, Coenzyme $Q_{10}$ is used at present as a medicament for treating congestive heart failure.

SUMMARY OF THE INVENTION

I have studied other medical indications of Coenzyme Q and have found, unexpectedly in view of the prior art, that Coenzymes Q are effective for the treatment of myasthenia.

The term "myasthenia" used in the present invention means various types of myasthenia, such as angiosclerotic myasthenia, myasthenia gastrica, myasthenia gravis, myasthenia gravis pseudoparalytica. myasthenia laryngis, and Coenzyme Q is particularly effective for the treatment of myasthenia gravis.

Myasthenia gravis is a syndrome of fatigue and exhaustion of the muscular system marked by progressive paralysis of muscles without sensory disturbance or atrophy. It may affect any muscle of the body, but especially those of the face, lips, tongue, throat and neck. Therefore, a fundamental remedy for myasthenia gravis comprises resting the whole body as much as possible. Medical therapy comprises mainly administration of a cholinesterase inhibitor. However, in using the cholinesterase inhibitor, control thereof is difficult. When the cholinesterase inhibitor is taken continuously or in a large amount, a serious harmful effect, i.e. production of cholinergic, is caused in many cases.

I have studied various drugs in order to search for an effective one that can be administered continuously for the treatment of myasthenia, and have found that Coenzyme Q represented by the following formula is effective for such treatment.

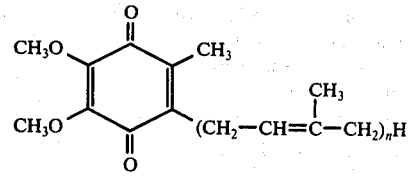

In the formula, $n$ represents an integer from 7 to 10.

An object of the present invention is to provide a method for the medical treatment of myasthenia with Coenzyme Q.

Another object of the present invention is to provide a novel drug or a medically useful formulation containing Coenzymes Q which can be continuously administered, without fear of significant side-effects, for the treatment of myasthenia.

Coenzyme Q used in the present invention, for example, Coenzyme $Q_{10}$ (the compound in which $n = 10$ in the above formula), can be mainly obtained synthetically, although it is possible to extract Coenzyme Q from animal organs. The physical and chemical properties of Coenzyme $Q_{10}$ produced synthetically are as follows:

1. Properties

Coenzyme $Q_{10}$ is yellow or orange crystalline powder; easily soluble in chloroform, benzene and carbon tetrachloride; soluble in acetone and ether; insoluble in ethanol; and hardly soluble in water and methanol.

2. Melting point

Approximately 48° C.

Further, the results of toxicity tests of Coenzyme $Q_{10}$ are as follows:

1. Acute toxicity test

In order to evaluate the acute toxicity of a single high dose administration of Coenzyme $Q_{10}$, male and female rats of Wistar strain and male and female mice of ICR-JCL strain were used, and oral, intramuscular, subcutaneous, and intravenous administrations were studied. For the oral administration of Coenzyme $Q_{10}$, gum Arabic suspension was used. For the intramuscular, subcutaneous and intravenous administrations, Coenzyme $Q_{10}$ was used as a solution containing a nonionic surfactant, Nikkol HCO-60. Nikkol HCO-60 is a trade mark of a non-ionic surfactant comprised of hydrogenated castor oil/polyoxyethylene-60 mole ether available from Nikko Chemicals, Co. Ltd., Japan.

Observation was carried out for 7 days by using six males and six females for each dose group. In any administration group, no change was recognized in the general condition, the body weight, the food intake, and the autopsy findings. As shown in the following Table 1, there was no case of deaths in rats and mice, at the maximum dose in each administration route.

Table 1

| Animal | Maximum dose (mg/Kg) by various routes | | | |
|---|---|---|---|---|
| Route | Oral | Intramuscular | Subcutaneous | Intravenous |
| Rats | 4000 | 500 | 500 | 250 |
| Mice | 4000 | 500 | 500 | 250 |

From the results described above, it can be concluded that the toxicity of Coenzyme $Q_{10}$ is extremely low and that $LD_{50}$ and Coenzyme $Q_{10}$ is far higher than the maximum dose mentioned above.

2. Subacute toxicity test a. Subacute oral toxicity test in rats

Coenzyme $Q_{10}$ was compulsorily and orally administered every day for 5 weeks to each group consisting of 10 male rats and 10 female rats of Wistar strain. The dose was 40, 200, and 1000 mg/Kg/day, respectively. Coenzyme $Q_{10}$ was used in the form of gum Arabic suspension, while the solution containing gum Arabic alone was used as the control group. Collection of blood and urine samples and autopsies were carried out 5 weeks after the initiation of administration.

By comparing the administration group with the control group, there was shown no difference in connection with the general condition and the body weight of the animals during the period of administration. With respect to 4 dead animals during the experiment, the autopsies revealed that they had spontaneous pneumonia and aspiration pneumonia due to the error of administration.

No significant change was recognized from the hematological test and the biochemical test of blood and urine.

In the morphological observation, there was no significant change in the weight of each organ. Further, in the macroscopical and histological observation by hematoxylin.Eosine staining and liver fat staining, abnormality was not recognized.

As described above, there was not recognized the toxicity seemingly due to the administration of Coenzyme $Q_{10}$ in the subacute oral toxicity test carried out for 5 weeks.

b. Subacute oral toxicity test in rabbits

Coenzyme $Q_{10}$ was compulsorily and orally administered every day for 23 days to each group consisting of 6 male rabbits and 5 female rabbits. The dose was 6, 60 and 600 mg/Kg/day, respectively. Coenzyme $Q_{10}$ was used in the form of gum Arabic suspension, whereas the solution containing gum Arabic alone was used as the control group. On the 24th day, blood samples were collected from all the animals, and 3 males and 2 females from each group were then selectively autopsied.

With reference to the general condition and the increase of body weight during the period of administration, there was shown no difference between the administration group and the control group. Abnormal findings were not obtained in the hematological test and the biochemical test of blood.

In the morphological observation, there was no effect on the weight of each organ. Further, abnormalities were not recognized in the macroscopical and histological observation by hematoxylin.Eosine staining and liver fat staining. Furthermore, in the electron-microscopic observation of liver carried out on the respective 7th, 14th, and 24th days after the adminstration, there were not recognized abnormal findings on the minute structure of the liver.

As mentioned above, there were not recognized the findings wherein the toxicity of Coenzyme $Q_{10}$ will be suggested in the subacute oral toxicity test carried out for 23 days.

3. Chronic oral toxicity test

Coenzyme $Q_{10}$ was compulsorily and orally administered to each group consisting of 10 male rats and 10 female rats of Wistar strain for consecutive 26 weeks in a ratio of 6 days a week. The dose was 6, 60 and 600 mg/Kg/day, respectively. Coenzyme $Q_{10}$ was used in the form of gum Arabic suspension, whereas the solution containing gum Arabic alone is used as the control group. Collection of blood and urine samples and autopsies were carried out 26 weeks after the administration.

With respect to the general condition of the animals during the period of administration, there was shown no difference between the administration group and the control group, and the body weight in the administration group increased the same as that of the control group.

During the experiment, 11 males and 3 females died of spontaneous pneumonia and aspiration pneumonia due to an erroneous administration.

From the standpoint of hematological findings, the leukocytal percentages showed some increase and decrease, but do not provide the mutual relation depending upon the dose; the percentages being within the range of physiological fluctuations.

No significant changes were recognized in the comparison of the administration group with the control group in the biochemical tests of blood and urine.

In the morphological observation, no significant increase and decrease in the weights of organs were shown. Further, abnormalities were not recognized in the macroscopical and histological observation by hemoxylin.Eosine staining and liver fat staining, when the administration group was compared with the control group.

As described above, no toxicity was observed in the chromic oral test of Coenzyme $Q_{10}$ carried out for 26 weeks.

4. Teratogenesis test

When the doses of 6, 60, and 600 mg/Kg/day of Coenzyme $Q_{10}$ were respectively administered to rats and mice, no adverse effects were noted in mothers, fetuses, and newborns.

As the results of the acute toxicity test, the subacute toxicity test, the chronic toxicity test, and the teratogenesis test, it was found that Coenzyme $Q_{10}$ used in the present invention was a very safe drug, without side-effects.

The effective amount of Coenzyme $Q_{10}$ in accordance with this invention varies depending on the types and symptoms of myasthenia, and usually a daily dose of about 5–100 mg can be administered to the human patient.

Coenzyme Q can be administered in any of the forms of powder, tablets, granules, capsules, injections, suppository, buccal drugs, and the like.

If Coenzyme Q is to be used in the form of a powder, it can be adsorbed on an excipient such as magnesium carbonate, silicic acid anhydride (for example, available under trade name of Siloid and Cuplex), synthetic aluminum silicate, calcium phosphate and the like, or by an organic excipient such as lactose, corn starch, crystalline cellulose (for example, Avicel), glucose, hydroxypropyl cellulose, and the like.

If Coenzyme Q is to be used in the form of tablets and capsules, the above-mentioned Coenzyme Q powder can be manufactured into tablets or capsules in a conventional manner. If Coenzyme Q is to be used in the form of an injectable liquid, it can be solubilized in water with a nonionic surfactant in accordance with any conventional method. As the nonionic surfactants, there may be mentioned hydrogenated castor oil/ethylene oxide addition products (for example, Nikkol HCO and Emalex HC), sorbitan fatty acid ester/ethylene oxide addition products (for example, Tween), alkylphenol/ethylene oxide addition product, fatty acid/ethylene oxide addition products, and sorbitan fatty acid esters (for example, Span).

When Coenzyme Q is used in the form of an injectable liquid, it can be mixed with the usual additives such as propylene glycol and glucose.

The effects of the present invention for the treatment of myasthenia gravis will be shown with reference to the results of clinical tests.

[I] Age 35, Female

She was attacked with myasthenia at the age of 21. She had a thymusectomy at the age of 22 and thereafter she took 60 mg/day of Ambenonium perorally continuously. Ambenonium is a cholinesterase inhibitor and available, for example, under the trademark Myterase. One year before the first medical examination in this hospital, she took 20 mg/day of Ambenonium.

At the first medical examination, drooping of the left eyelid, disorder in the movement of the left eyeball and fatiguing of the limbs were observed. By continuous peroral administration of 20 mg/day of Ambenonium for 4 months, no significant improvement in the symptoms was recognized. On the next day, at the start of the peroral administration of 30 mg/day of Coenzyme $Q_{10}$ in combination with Ambenonium, an improvement in walking and relief in a feeling of difficulty in breathing were recognized. The administration according to the recipe was continued for 30 days and, thereafter, dosage of Ambenonium was reduced to 10 mg/day (morning and evening: 5 mg each). This treatment was continued for a further period of 30 days. After the treatment, long distance walking and light work became possible. Dosage of Ambenonium was further reduced to 5 mg/day but no worsening of the symptoms was caused and the patient is now getting better.

[II] Age 30, Female

The patient was attacked with myasthenia at the age of 18 and had a thymusectomy at the age of 19. Thereafter, she took 20–25 mg/day of Ambenonium perorally intermittently.

At the first medical examination, eye symptoms such as eyelid drooping and double vision and evervation in limbs were remarkable. As for the walking ability, she barely walked 100 m even when the effect of Ambenonium was exerted.

By peroral administration of 25 mg/day of Ambenonium and 30 mg/day of Coenzyme $Q_{10}$, muscular contraction was caused 2–3 days after the start of the treatment. Dosage of Ambenonium was reduced to 20 mg/day. After the treatment was continued according to this recipe for one week, the heavy feeling of the body, double vision and the eye symptoms were relieved. Continuous 400 m walking was made possible.

[III] Age 65, Male

The patient was attacked by myasthenia at the age of 61. At the first medical examination, only eyelid drooping (eye fissure: left 5 mm, right 2 mm) was observed. Peroral administration of 10 mg/day of a cholinesterase inhibitor (Distigmine Bromide) and application of a dropping lotion (0.5 % aqueous Distigmine Bromide solution) in the eyes morning and evening were continued for 6 months and the symptoms were improved a little (eye fissure: left 6 mm, right 4 mm).

30 mg/day of Coenzyme $Q_{10}$ was administered perorally in combination with the above medicaments to improve and to stabilize the opening of the eyelids. The administration of the dropping lotion became unnecessary. Though it was difficult for the patient to walk straight looking ahead before the administration of Coenzyme $Q_{10}$, he could walk easily after the treatment. It was a remarkable improvement that he could ascend and descend stairs easily.

The following are the examples of effective pharmaceutical preparations for the administration of the Coenzyme Q in the present invention, but the invention is not limited thereto.

Example 1

Capsules:

| | |
|---|---|
| Coenzyme $Q_{10}$ | 5 g |
| Microcrystalline cellulose | 80 g |
| Corn starch | 20 g |
| Lactose | 22 g |
| Polyvinylpyrrolidone | 3 g |
| Total | 130 g |

The above composition was shaped into granules in a usual manner and charged in gelatin hard capsules.

Example 2

Powders:

| | |
|---|---|
| Coenzyme $Q_{10}$ | 50 g |
| Microcrystalline cellulose | 400 g |
| Corn starch | 550 g |
| Total | 1000 g |

Coenzyme $Q_{10}$ was dissolved in acetone and the solution was adsorbed on the microcrystalline cellulose and dried. It was then mixed with the corn starch to obtain a powdery product in a usual manner.

Example 3

Tablets:

| | |
|---|---|
| Coenzyme $Q_{10}$ | 5 g |
| Corn starch | 10 g |
| Refined white sugar | 20 g |
| Carboxymethyl cellulose calcium | 10 g |
| Microcrystalline cellulose (Avicel) | 40 g |
| Polyvinylpyrrolidone (K-30) | 5 g |
| Talc | 10 g |
| Total | 100 g |

Coenzyme $Q_{10}$ was dissolved in acetone and then the solution was adsorbed on the microcrystalline cellulose and dried. It was then mixed with the corn starch, refined white sugar and carboxymethyl cellulose calcium. Then, an aqueous solution of polyvinylpyrrolidone was added thereto as binder. The mixture was shaped into granules in a usual manner. The granules were mixed with talc as lubricant and then shaped into 100 mg tablets.

Example 4

Injections:

| | | |
|---|---|---|
| Coenzyme $Q_{10}$ | | 10 g |
| Nikkol HCO-60 | | 37 g |
| Sesame oil | | 2 g |
| Sodium chloride | | 9 g |
| Propylene glycol | | 40 g |
| Phosphate buffer (0.1M, pH 6.0) | | 100 ml. |
| Distilled water | ad | 1000 ml. |

Coenzyme $Q_{10}$, Nikkol HCO-60, sesame oil and a half of the propylene glycol were mixed together and the mixture was heated to about 80° C and thereby dissolved.

The distilled water wherein the phosphate buffer, sodium chloride and propylene glycol had been dissolved previously was heated to about 80° C and added to the former solution to obtain 1000 ml. of an aqueous solution. The aqueous solution was charged in 1 ml. ampoules and the ampoules were sealed by fusion and sterilized by heating.

EXAMPLE 5

Capsules were produced in the same way as Example 1, except for the substitution of Coenzyme $Q_9$ in Example 1 for Coenzyme $Q_{10}$.

EXAMPLE 6

An injectable solution was produced in the same way as Example 4, except for the substitution of Coenzyme $Q_9$ for Coenzyme $Q_{10}$.

The embodiments of the invention in which an exclusive property or privilege is claimed are defined as follows:

1. A method for the treatment of myasthenia which comprises administering to a human suffering from myasthenia a therapeutically effective amount of Coenzyme Q having the formula:

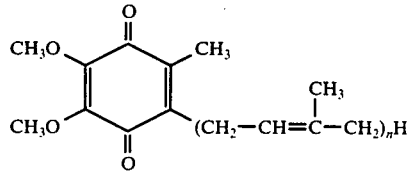

wherein $n$ is an integer from 7 to 10.

2. A method as claimed in claim 1, wherein $n$ is 10.

3. A method as claimed in claim 1, wherein the myasthenia is myasthenia gravis.

4. A method as claimed in claim 1, wherein said therapeutically effective amount is a daily dose of from 5 to 100 mg of said Coenzyme Q, administered orally.

5. A method as claimed in claim 1, wherein said therapeutically effective amount is a daily dose of from 5 to 100 mg of said Coenzyme Q, administered by injection.

* * * * *